(12) United States Patent
Simon

(10) Patent No.: US 6,346,256 B1
(45) Date of Patent: Feb. 12, 2002

(54) STABLE O/W/O EMULSION AND ITS USE AS A COSMETIC AND/OR DERMATOLOGICAL COMPOSITION

(75) Inventor: Pascal Simon, Vitry sur Seine (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/384,430

(22) Filed: Aug. 27, 1999

(30) Foreign Application Priority Data

Sep. 9, 1998 (FR) .............................. 98 11263

(51) Int. Cl.⁷ .......................... A61K 7/00; A61K 7/48; A61K 7/075
(52) U.S. Cl. ................. 424/401; 424/70.12; 424/70.19; 424/70.31; 514/844; 514/846; 514/847; 514/938; 514/944; 514/945
(58) Field of Search ............................ 424/401, 70.12, 424/70.19, 70.31; 574/844, 846, 847, 938, 944, 945

(56) References Cited

U.S. PATENT DOCUMENTS 5,034,228 A * 7/1991 Meybeck et al.
5,391,321 A * 2/1995 Gruning et al.
5,412,004 A * 5/1995 Tachibana et al.
5,445,823 A * 8/1995 Hall et al.
5,811,487 A * 9/1998 Schulz, Jr. et al.
5,962,015 A * 10/1999 Delrieu et al.

FOREIGN PATENT DOCUMENTS

EP      0 559 013      9/1993

* cited by examiner

Primary Examiner—Diana Dudash
Assistant Examiner—Alysia Berman
(74) Attorney, Agent, or Firm—Oblon, Spivak, McClelland, Maier & Neustadt, P.C.

(57) ABSTRACT

An oil/water/oil triple emulsion is stabilized with at least one partially or completely crosslinked organopolysiloxane elastomer having at least one polyoxyethylenated and/or polyoxypropylenated chain. The stable triple emulsion can be used as a composition for topical application, in particular as a cosmetic or dermatological composition, and especially as a vehicle for active principles. The emulsion is particularly useful for cleansing and/or treating and/or protecting the skin and/or mucous membranes and/or keratinous fibers.

16 Claims, No Drawings

STABLE O/W/O EMULSION AND ITS USE AS A COSMETIC AND/OR DERMATOLOGICAL COMPOSITION

BACKGROUND OF THE INVENTION

Field of the Invention

The present invention relates to a stable oil/water/oil triple emulsion and to its use, in particular in the cosmetics and/or dermatological fields, especially for the controlled release of active principles, for the purpose in particular of cleansing, treating, protecting and/or moisturizing the skin and/or mucous membranes and/or keratinous fibers and more particularly for the purpose of treating dry skin.

The use of topical compositions in the form of emulsions is known, in particular in the fields of cosmetics and dermatology. These emulsions are generally oil-in-water (O/W) or water-in-oil (W/O) emulsions, or multiple emulsions of the water/oil/water (W/O/W) or oil/water/oil (O/W/O) type. Preferably, multiple emulsions with an aqueous external phase, namely W/O/W emulsions, are used. These W/O/W emulsions combine the advantages of freshness on application, due to the water present in the aqueous external phase, and of comfort, due to the relatively large amount of oil.

However, O/W/O emulsions are also advantageous because of their oily continuous phase, making it possible to form, at the surface of the skin, a lipid film which prevents transepidermal water loss and protects the skin from external attack. In addition, the greasy effect of such emulsions can be avoided by incorporating therein novel light oils which are non-greasy to the touch, such as, for example, low-viscosity silicone oils or certain esters of fatty acids and of fatty alcohols with a short chain. It is therefore advantageous to have available multiple emulsions of the O/W/O type.

However, multiple emulsions are generally not exploited to any great extent because they frequently exhibit problems with stability over time. The most frequently encountered mechanism for destabilization is the migration of oil from the internal droplets to the oily external phase through the intermediate aqueous layer, either by simple diffusion of oil through the aqueous membrane or by prior rupture of the aqueous film, which causes the coalescence of the internal droplets of oil and results in a release of oil into the oily external phase. Generally, this phenomenon, known as loss of the multiple nature, ends up by bringing about macroscopically visible phase separation and the production of an unstable, simple O/W emulsion in place of a triple emulsion.

Various approaches have consequently been envisaged to mitigate this disadvantage. In particular, one approach consists of introducing, into the oily internal or external phase, one or more gelling polymer(s), the role of which is to limit, on a long-term basis, the movements of oil from the internal phase to the external phase. However, polymers capable of gelling oils are not very common and do not have good cosmetic properties: they intensify the feeling of greasiness and are sticky during and after application to the skin. The multiple emulsions obtained exhibit the drawback of being sticky and of taking a long time to penetrate into the skin.

The need therefore remains for a stable O/W/O multiple emulsion which does not have the disadvantages of those of the prior art and which is, in particular, pleasant to use on the skin.

SUMMARY OF THE INVENTION

The Applicant has now found, unexpectedly, that the use of a partially or completely crosslinked organopolysiloxane elastomer comprising a polyoxyethylenated and/or polyoxypropylenated chain makes it possible to obtain a stable O/W/O multiple emulsion without requiring the addition of other stabilizing agents.

DETAILED DESCRIPTION OF THE INVENTION

The subject-matter of the present invention is an O/W/O triple emulsion comprising at least one oily phase and a water phase, characterized in that the triple emulsion comprises at least one partially or completely crosslinked organopolysiloxane elastomer comprising a polyoxyethylenated and/or polyoxypropylenated chain.

Hereinafter, the triple emulsions of the present invention will be described as comprising an oil-in-water primary emulsion and an oily external phase. However, triple emulsion refers to a unique type of emulsion which is distinct from an O/W or W/O emulsion.

Another subject-matter of the present invention is the use of at least one partially or completely crosslinked organopolysiloxane elastomer comprising a polyoxyethylenated and/or polyoxypropylenated chain for the stabilization of an oil/water/oil triple emulsion.

The triple emulsion according to the invention has the advantage of being stable and of being able to retain the activity of active principles, in particular of lipophilic active principles, present in the oily internal phase, whence they are released during the application of the composition to the skin, mucous membranes and/or hair.

The partially or completely crosslinked organopolysiloxane elastomers which can be used in the emulsion according to the present invention can be introduced into either of the oily phases. They are preferably introduced into the oily external phase of the emulsion. The partially or completely crosslinked organopolysiloxane elastomers are generally emulsifiers. They can be chosen in particular from the crosslinked polymers disclosed in Application EP-A-0,545,002, indicated here by way of reference. These organopolysiloxanes are obtained by addition polymerization (for example, by hydrosilation) of the following compounds (I) and (II):

(I) an organohydropolysiloxane of formula (1):

(1)

in which $R^1$ represents a substituted or unsubstituted alkyl, aryl or aralkyl group comprising from 1 to 18 carbon atoms or a halogenated hydrocarbon-comprising group; $R^2$ represents a group:

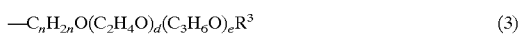

(3)

in which $R^3$ is a hydrogen, a saturated aliphatic hydrocarbon-comprising group having from 1 to 10 carbon atoms or a —(CO)—$R^5$ group where $R^5$ is a saturated aliphatic hydrocarbon-comprising group having from 1 to 5 carbon atoms; d is an integer from 2 to 200 and e is an integer from 0 to 200, provided that d+e is a number ranging from 3 to 200, and n is a number from 2 to 6, a is a value satisfying the inequality:

$1.0 \leq a \leq 2.5$, b is a value satisfying the inequality: $0.001 \leq b \leq 1.0$ and c is a value satisfying the inequality: $0.001 \leq c \leq 1.0$;

or an organohydropolysiloxane represented by the following formula (2):

$$R^1{}_f H_g SiO_{(4-f-g)/2} \quad (2)$$

in which $R^1$ has the same meaning as in the formula (1), f is a value satisfying the inequality: $1.0 \leq f \leq 3.0$ and g is a value satisfying the inequality: $0.001 \leq g \leq 1.5$;

or a mixture of the organohydropolysiloxanes of formulae (1) and (2), and (II) a polyoxyalkylene represented by the following formula (A):

$$C_m H_{2m} O(C_2 H_4 O)_h (C_3 H_6 O)_i C_m H_{2m-1} \quad (A)$$

in which h is an integer ranging from 2 to 200, i is an integer ranging from 0 to 200, provided that h+i is a number ranging from 3 to 200, and m is a number ranging from 2 to 6, or an organopolysiloxane represented by the following formula (B):

$$R^1{}_j R^4{}_k SiO_{(4-g-k)/2} \quad (B)$$

in which $R^1$ has the same meaning as in the formula (1), $R^4$ is a monovalent hydrocarbon-comprising group having an unsaturated aliphatic bond at the end and comprising 2 to 10 carbon atoms, j is a value satisfying the inequality: $1.0 \leq j \leq 3.0$ and k is a value satisfying the inequality: $0.001 \leq k \leq 1.5$, or a mixture of the polyoxyalkylene of formula (A) and of the organopolysiloxane of formula (B), where at least one organohydropolysiloxane of formula (1) or at least one polyoxyalkylene of formula (A) is present as essential component of the addition polymerization.

The organopolysiloxane is preferably mixed with a silicone oil and/or a polyol and is prepared directly as such a mixture. The silicone oil preferably exhibits a viscosity equal to or less than 100 cSt at 25° C. For example, the silicone oil can have a viscosity at 25° C. of 95, 90, 85, 80, 75, 70, 65, 60, 55, 50, 45, 40, 35, 30, 25, 20, 15, 10, 9, 8, 7, 6, 5, 4, 3, 2, and 1 cSt, inclusive of all values and subranges therebetween. According to one embodiment of the invention, the organopolysiloxane elastomer is prepared from 100 parts by weight of the constituents defined above and 3 to 200 parts by weight of a silicone oil having a viscosity equal to or less than 100 cSt at 25° C. and/or of a polyol. The silicone oil can be a volatile or non-volatile silicone oil or a mixture of volatile silicone oil and of non-volatile silicone oil.

For example, the partially or completely crosslinked organopolysiloxane comprising a polyoxyethylenated and/or polyoxypropylenated chain may be the product sold by Shin-Etsu under the name of KSG 21. This product comprises 28% of organopolysiloxane and 72% of silicone oil having a viscosity of 6 cSt.

In the triple emulsion according to the invention, the partially or completely crosslinked organopolysiloxane is preferably used in an amount of active material ranging from 0.1 to 10% and preferably from 1 to 5% by weight with respect to the total weight of the triple emulsion.

The O/W primary emulsion preferably comprises one or more emulsifiers chosen from:

(1) nonionic surfactants having an HLB of greater than or equal to 11, optionally in combination with a lipophilic co-surface-active agent, such as a fatty alcohol, a fatty acid or a glyceryl fatty ester (glyceryl stearate). For example, the nonionic surfactant having an HLB of greater than or equal to 11 may be oxyethylenated esters of fatty acids and of glycerol, oxyethylenated esters of fatty acids and of sorbitan, oxyethylenated fatty acids, sugar esters, such as sucrose stearate, and their mixtures;

(2) polymers capable of stabilizing an O/W emulsion. For example, polymers of this type may be copolymers composed of a major fraction (i.e., >50 mole %, based on the total moles of monomer in the copolymer) of mono-olefinically unsaturated $C_3$–$C_6$ carboxylic acid monomer, or anhydrides thereof, and of a minor fraction (i.e., <50 mole %, based on the total moles of monomer in the copolymer) of acrylic acid fatty ester monomer, such as the product sold under the name Pemulen TR2 by Goodrich (CTFA name: acrylates/C10-30 alkyl acrylate crosspolymer), or polyacrylamides, such as the product sold under the name Hostacerin AMPS by Hoechst (CTFA name: Ammonium polyacryldimethyltauramide), and their mixtures;

(3) dispersions of lipid vesicles based on ionic amphiphilic lipids (liposomes) or nonionic amphiphilic lipids, and in particular liposomes based on the hydrogenated lecithin/oxyethylenated soya sterol combination.

Mixture of these emulsifiers may also be used.

These emulsifiers can be introduced into the aqueous phase or into the oily phase of the primary emulsion. The amount of emulsifier(s) in the primary emulsion varies according to the nature of the emulsifiers used. It can be used, for example, at concentrations of 0.1, 0.5, 1, 2, 3, 4, 5, 6, 7, 8, 9, 10, 11, 12, 13, 14, and 15% by weight, inclusive of all values and subranges therebetween, preferably in the range of 0.1 to 15% by weight with respect to the total weight of the primary emulsion.

The amount of O/W primary emulsion in the triple emulsion is generally 50, 55, 60, 65, 70, 75, 80, 85, 90, and 95%, inclusive of all values and subranges therebetween, preferably in the range of from 50 to 95% and more preferably from 70 to 85% by weight with respect to the total weight of the triple emulsion.

The amount of the oily internal phase is generally 0.1, 0.5, 1, 5, 10, 15, 20, 25, 30, 35, and 40% by weight, inclusive of all values and subranges therebetween, preferably in the range of from 0.1 to 40% and more preferably from 1 to 25% by weight with respect to the total weight of the triple emulsion. The amount of the aqueous phase is generally 10, 15, 20, 25, 30, 35, 40, 45, 50, 55, 60, 65, 70, 75, 80, 85, and 90%, inclusive of all values and subranges therebetween, preferably in the range of from 10 to 90% and more preferably from 40 to 80% by weight with respect to the total weight of the triple emulsion.

The oily phase of the O/W primary emulsion and the oily external phase comprise one or more fatty substances chosen from oils of animal origin, oils of vegetable origin (for example, apricot kernel oil, liquid fraction of karite butter), mineral oils (for example, liquid petrolatum), synthetic oils (for example, isohexadecane, hydrogenated polyisobutene or Parleam oil), fluorinated oils, silicone oils and in particular volatile silicone oils, such as octylheptamethyltrisiloxane (or caprylylmethicone) and cyclomethicones, for example cyclopentasiloxane and cyclohexasiloxane, waxes and in particular silicone waxes, silicone gums or silicone resins.

The oily phase comprising the organopolysiloxane elastomer and in particular the oily external phase of the O/W/O multiple emulsion preferably comprises, as fatty substance, at least one solvent for the organopolysiloxane elastomer which is preferably a silicone oil chosen from cyclic organopolysiloxanes (cyclomethicone), such as cyclohexamethylsiloxane, or low-viscosity linear organopolysiloxanes (polydimethylsiloxanes with a viscosity of less than 50 cSt or dimethicones).

The triple emulsion is prepared conventionally by preparation of the primary emulsion and incorporation of a predetermined amount of the primary emulsion in the oily external phase which, according to a preferred embodiment of the invention, comprises the partially or completely crosslinked organopolysiloxane elastomer comprising a polyoxyethylenated and/or polyoxypropylenated chain.

The triple emulsion according to the invention can be used in particular in the cosmetics, dermatological and pharmaceutical fields. It is preferably intended to constitute a composition for topical application. In this case, the composition must comprise a topically acceptable medium: a medium compatible with the skin, mucous membranes, nails, scalp and/or hair. As indicated at the beginning of the description, one of the major advantages of the emulsion in accordance with the invention is that the emulsion can contain both cosmetic and therapeutic active principles while remaining stable. It is therefore possible for these active principles to be chosen in particular from all those commonly used in the field of cosmetics, dermatology or medicine.

In particular, the active principle can be a lipophilic active principle, but it can also be hydrophilic and, depending on its nature, it can be introduced into one of the oily phases or into the aqueous phase of the triple emulsion according to the invention.

For example, lipophilic active principles can include lipophilic vitamins, such as vitamin A (retinol), vitamin D, vitamin E (tocopherol), vitamin K and the derivatives of these vitamins, such as the esters; ceramides; non-saponifiable materials, such as karite non-saponifiable material; algal extracts, in particular those rich in polyunsaturated fatty acids, such as eicosapentaenoic acid and docosahexaenoic acid; or unsaturated oils, for example fish oils rich in linoleic and linolenic acids.

Hydrophilic active principles may be, for example, polyols, such as glycerol, glycols and sugar derivatives; enzymes; natural extracts; procyanidol oligomers; vitamins, such as vitamin C and its derivatives such as the esters; urea; depigmenting agents, such as kojic acid and caffeic acid; beta-hydroxy acids, such as salicylic acid and its derivatives; alpha-hydroxy acids, such as lactic acid and glycolic acid; moisturizers, such as protein hydrolysates; softeners, such as allantoin; and their mixtures.

The active principle is present in an amount effective to provide the expected result. For example, it can be present in the emulsion at a concentration of 0.01, 0.05, 0.1, 0.5, 1, 2, 5, 10, 15, and 20%, inclusive of all values and subranges therebetween, preferably in an amount ranging from 0.01 to 20%, more preferably from 0.1 to 10% and most preferably from 0.5 to 5% by weight with respect to the total weight of the composition.

The O/W/O emulsions according to the invention can constitute in particular compositions for cleansing, protecting, treating and/or caring for the skin, mucous membranes and/or hair, in particular for the face, for the neck, for the hands, for the hair, for the scalp or for the body, as well as for the eyelashes. They can constitute in particular protective, treatment or care creams for the face, for the hands or for the feet, protective or care body milks, or lotions, gels or foams for caring for the skin, mucous membranes, hair and scalp. The compositions of the invention are particularly appropriate for moisturizing the skin and/or treating dry skin.

A further subject-matter of the invention is consequently the cosmetic use of the emulsion as defined above for cleansing and/or treating and/or protecting and/or moisturizing the skin and/or mucous membranes and/or keratinous fibers, that is to say the hair and/or eyelashes.

Another subject-matter of the invention is the use of the emulsion as defined above for the preparation of a dermatological composition intended to treat and/or protect dry skin.

Another subject-matter of the invention is a cosmetic and/or dermatological process for cleansing and/or treating and/or protecting and/or moisturizing the skin, mucous membranes and/or keratinous fibers, characterized in that it consists in applying an emulsion as defined above to the skin, mucous membranes and/or keratinous fibers.

The composition of the invention can also comprise lipophilic or hydrophilic adjuvants which are standard in the cosmetics and dermatological fields, such as foaming surfactants, preservatives, antioxidants, sequestering agents, solvents (for example, octyldodecanol), fragrances, fillers, sunscreen agents, odor absorbers, coloring materials, gelling agents and lipid vesicles.

The composition of the invention can also include gelling agents, of, for example, clays, polysaccharide gums and their derivatives (for example, xanthan gum, carboxymethylhydroxypropyl guar), or carboxyvinyl polymers (carbomer or sodium carbomer).

The amounts of these various adjuvants are those conventionally used in the fields under consideration, for example, 0.01, 0.05, 0.1, 0.2, 0.5, 1, 2, 3, 4, 5, 6, 7, 8, 9, 10, 11, 12, 13, 14, and 15% by weight, inclusive of all values and subranges therebetween, preferably from 0.01 to 15% of the total weight of the composition. The nature of the adjuvants and their amounts must be such that they do not modify the properties of the compositions according to the invention.

The adjuvants, depending on their nature, can be introduced into the aqueous phase or into one of the oily phases of the triple emulsion.

Obviously, numerous modifications and variations on the present invention are possible in light of the above teachings. It is therefore to be understood that within the scope of the appended claims, the invention may be practiced otherwise than as specifically described herein.

Having generally described this invention, a further understanding can be obtained by reference to certain specific examples which are provided herein for purposes of illustration only, and are not intended to be limiting unless otherwise specified. The amounts are given therein as % by weight with respect to the total weight of the composition.

EXAMPLES

Example 1

Moisturizing Night Cream

1. O/W primary emulsion:

| Phase A: Preparation of liposomes | |
|---|---|
| Hydrogenated lecithin (Lecinol S 10, sold by Nikkol) | 0.72% |
| Oxyethylenated soya sterols (Generol 122 N E 5D, sold by Henkel) | 2.8% |
| Water | 9% |
| Phase B: Oily phase of the O/W primary emulsion | |
| Isohexadecane | 3.5% |
| Apricot kernal oil | 5% |
| Karite non-saponifiable materials | 1% |
| Fragrance | 0.5% |
| Preservative | 0.6% |
| Phase C: Aqueous phase | |
| Glycerol | 3% |
| Preservative | 0.2% |
| Xanthan gum | 0.2% |
| Sodium carbomer | 0.15% |
| Water | 53.33% |

-continued

2. Oily external phase:

| | |
|---|---|
| Cyclohexasiloxane | 12% |
| KSG 21, comprising 28% of active material | 8% |

Example 2

Nourishing Cream for Dry Skin

1. O/W primary emulsion:

Phase A:

| | |
|---|---|
| Glyceryl stearate and PEG-100 glyceryl stearate (Arlacel 165, sold by ICI) | 1.8% |
| Polysorbate 60 (Tween 60, sold by ICI) | 0.75% |
| Liquid fraction of karite butter | 7.3% |
| Cetyl alcohol | 1.75% |
| Cyclopentasiloxane (DC Fluid 245, sold by Dow Corning) | 7% |
| Parleam oil | 4% |
| Fragrance | 0.5% |
| Preservative | 0.6% |

Phase B:

| | |
|---|---|
| Glycerol | 7% |
| Preservative | 0.2% |
| Xanthan gum | 0.1% |
| Sodium carbomer | 0.2% |
| Water | 53.8% |

2. Oily external phase:

| | |
|---|---|
| Dimethicone 10 cSt (DC Fluid 200, sold by Dow Corning) | 10% |
| KSG 21, comprising 28% of active material | 8% |

Example 3

Moisturizing Cream

1. O/W primary emulsion:

Phase A:

| | |
|---|---|
| Octyldodecanol | 2% |
| Cyclopentasiloxane (DC Fluid 245, sold by Dow Corning) | 4.5% |
| Tocopheryl acetate | 1% |
| Fragrance | 0.5% |
| Preservative | 0.6% |

Phase B:

| | |
|---|---|
| Glycerol | 5.5% |
| Preservative | 0.2% |
| Acrylates/C10–30 alkyl acrylate crosspolymer (Pemulen TR 2, sold by Goodrich) | 0.13% |
| Ammonium polyacryldimethyltauramide (Hostacerin AMPS, sold by Hoechst) | 1.1% |
| Water | 69.47% |

2. Oily external phase:

| | |
|---|---|
| Caprylylmethicone (Silsoft 034, sold by Witco) | 7% |
| KSG 21, comprising 28% of active material | 8% |

We claim:

1. An oil/water/oil triple emulsion comprising oil, water, and
at least one partially or completely crosslinked organopolysiloxane elastomer, wherein said organopolysiloxane elastomer contains at least one substituent chain selected from the group consisting of polyoxyethylene, polyoxypropylene, copolymers of polyoxyethylene and polyoxypropylene, and mixtures thereof.

2. The emulsion of claim 1, wherein said organopolysiloxane elastomer is obtained by addition polymerization of the following compounds (I) and (II):

(I) an organohydropolysiloxane of formula (1):

$$R^1_a R^2_b H_c SiO_{(4-a-b-c)/2} \quad (1)$$

in which $R^1$ represents a substituted or unsubstituted allyl, aryl or aralkyl group comprising from 1 to 18 carbon atoms or a halogenated hydrocarbon-comprising group; $R^2$ represents a group:

$$-C_n H_{2n} O(C_2 H_4 O)_d (C_3 H_6 O)_e R^3 \quad (3)$$

in which $R^3$ is a hydrogen, a saturated aliphatic hydrocarbon-comprising group having from 1 to 10 carbon atoms or a $-(CO)-R^5$ group where $R^5$ is a saturated aliphatic hydrocarbon-comprising group having from 1 to 5 carbon atoms; d is an integer from 2 to 200 and e is an integer from 0 to 200, provided that d+e is a number ranging from 3 to 200, and n is a number from 2 to 6, a is a value satisfying the inequality:

$1.0 \leq a \leq 2.5$, b is a value satisfying the inequality: $0.001 \leq b \leq 1.0$ and c is a value satisfying the inequality: $0.001 \leq c \leq 1.0$;

or an organohydropolysiloxane represented by the following formula (2):

$$R^1_f H_g SiO_{(4-f-g)/2} \quad (2)$$

in which $R^1$ has the same meaning as in the formula (1), f is a value satisfying the inequality:
$1.0 \leq f \leq 3.0$ and g is a value satisfying the inequality: $0.001 \leq g \leq 1.5$;
or a mixture of the organohydropolysiloxanes of formulae (1) and (2), and (II) a polyoxyalkylene represented by the following formula (A):

$$C_m H_{2m} O(C_2 H_4 O)_h (C_3 H_6 O)_i C_m H_{2m-1} \quad (A)$$

in which h is an integer ranging from 2 to 200, i is an integer ranging from 0 to 200, provided that h+i is a number ranging from 3 to 200, and m is a number ranging from 2 to 6, or an organopolysiloxane represented by the following formula (B):

$$R^1_j R^4_k SiO_{(4-j-k)/2} \quad (B)$$

in which $R^1$ has the same meaning as in the formula (1), $R^4$ is a monovalent hydrocarbon-comprising group having an unsaturated aliphatic bond at the end and comprising 2 to 10 carbon atoms, j is a value satisfying the inequality: $1.0 \leq j \leq 3.0$ and k is a value satisfying the inequality: $0.001 \leq k \leq 1.5$,
or a mixture of the polyoxyalkylene of formula (A) and of the organopolysiloxane of formula (B), where at least one organohydropolysiloxane of formula (1) or at least one polyoxyalkylene of formula (A) is present as essential component of the addition polymerization.

3. The emulsion of claim 1, wherein said organopolysiloxane elastomer is mixed with a silicone oil and/or a polyol.

4. The emulsion of claim 1, wherein said organopolysiloxane elastomer is present in an amount ranging from 0.1 to 10% by weight with respect to the total weight of the triple emulsion.

5. The emulsion of claim 1, further comprising one or more emulsifiers selected from the group consisting of nonionic surfactants having an HLB of greater than or equal to 11, polymers capable of stabilizing an oil-in-water emulsion, dispersions of lipid vesicles, and mixtures thereof.

6. The emulsion of claim 5, wherein said nonionic surfactant comprises surfactants selected from the group consisting of oxyethylenated esters of fatty acids, oxyethylenated esters of glycerol, oxyethylenated esters of sorbitan, esters of sugars, and mixtures thereof.

7. The emulsion of claim 5, wherein said dispersion of lipid vesicles is a dispersion of liposomes.

8. The emulsion of claim 1, further comprising at least one active principle selected from the group consisting of vitamins, ceramides, non-saponifiable materials, algal extracts, unsaturated oils, polyols, enzymes, natural extracts, procyanidol oligomers, urea, depigmenting agents, beta-hydroxy acids, alpha-hydroxy acids, moisturizers, softeners, and mixtures thereof.

9. The emulsion of claim 8, wherein said active principle ranges from 0.01 to 20% by weight with respect to the total weight of the triple emulsion.

10. The emulsion of claim 1, further comprising at least one lipophilic or hydrophilic adjuvant selected from the group consisting of preservatives, antioxidants, sequestering agents, solvents, fragrances, fillers, sunscreen agents, odor absorbers, coloring materials, gelling agents and lipid vesicles, and mixtures thereof.

11. A method of treating human skin, mucous membranes, or keratinous fibers comprising applying the emulsion of claim 1 to said skin, mucous membranes, or keratinous fibers.

12. A method of stabilizing an oil/water/oil triple emulsion, comprising:
adding to an oil/water/oil triple emulsion at least one partially or completely crosslinked organopolysiloxane elastomer having at least one substituent chain selected from the group consisting of polyoxyethylene, polyoxypropylene, copolymers of polyoxyethylene and polyoxypropylene, and mixtures thereof.

13. The method of stabilizing an oil/water/oil triple emulsion of claim 12, wherein said organopolysiloxane elastomer is obtained by addition polymerization of the following compounds (I) and (II):
(I) an organohydropolysiloxane of formula (1):

$$R^1_a R^2_b H_c SiO_{(4-a-b-c)/2} \quad (1)$$

in which $R^1$ represents a substituted or unsubstituted alkyl, aryl or aralkyl group comprising from 1 to 18 carbon atoms or a halogenated hydrocarbon-comprising group; $R^2$ represents a group:

$$-C_nH_{2n}O(C_2H_4O)_d(C_3H_6O)_eR^3 \quad (3)$$

in which $R^3$ is a hydrogen, a saturated aliphatic hydrocarbon-comprising group having from 1 to 10 carbon atoms or a —(CO)—$R^5$ group where $R^5$ is a saturated aliphatic hydrocarbon-comprising group having from 1 to 5 carbon atoms; d is an integer from 2 to 200 and e is an integer from 0 to 200, provided that d+e is a number ranging from 3 to 200, and n is a number from 2 to 6, a is a value satisfying the inequality:

$1.0 \leq a \leq 2.5$, b is a value satisfying the inequality: $0.001 \leq b \leq 1.0$ and c is a value satisfying the inequality: $0.001 \leq c \leq 1.0$;

or an organohydropolysiloxane represented by the following formula (2):

$$R^1_f H_g SiO_{(4-f-g)/2} \quad (2)$$

in which $R^1$ has the same meaning as in the formula (1), f is a value satisfying the inequality: $1.0 \leq f \leq 3.0$ and g is a value satisfying the inequality: $0.001 \leq g \leq 1.5$;

or a mixture of the organohydropolysiloxanes of formulae (1) and (2), and
(II) a polyoxyallylene represented by the following formula (A):

$$C_mH_{2m}O(C_2H_4O)_h(C_3H_6O)_iC_mH_{2m-1} \quad (A)$$

in which h is an integer ranging from 2 to 200, i is an integer ranging from 0 to 200, provided that h+i is a number ranging from 3 to 200, and m is a number ranging from 2 to 6, or an organopolysiloxane represented by the following formula (B):

$$R^1_j R^4_k SiO_{(4-j-k)/2} \quad (B)$$

in which $R^1$ has the same meaning as in the formula (1), $R^4$ is a monovalent hydrocarbon-comprising group having an unsaturated aliphatic bond at the end and comprising 2 to 10 carbon atoms, j is a value satisfying the inequality: $1.0 \leq j \leq 3.0$ and k is a value satisfying the inequality: $0.001 \leq k \leq 1.5$, or a mixture of the polyoxyalkylene of formula (A) and of the organopolysiloxane of formula (B), where at least one organohydropolysiloxane of formula (1) or at least one polyoxyalkylene of formula (A) is present as essential component of the addition polymerization.

14. The emulsion of claim 3, wherein the silicone oil has a viscosity equal to or less than 100 cSt at 25° C.

15. The emulsion of claim 5, wherein said polymer is a copolymer selected from the group consisting of copolymers containing a major fraction of a mono-olefinically unsaturated $C_3$–$C_6$ carboxylic acid monomer or a mono-olefinically unsaturated $C_3$–$C_6$ carboxylic acid anhydride monomer, and containing a minor fraction of an acrylic acid fatty ester monomer, polyacrylamides, and mixtures thereof.

16. The emulsion of claim 1, wherein said oil comprises one or more fatty substances selected from the group consisting of oils of animal origin, oils of vegetable origin, mineral oils, synthetic oils, silicone oils, fluorinated oils, waxes, silicone gums and silicone resins.

* * * * *

UNITED STATES PATENT AND TRADEMARK OFFICE
CERTIFICATE OF CORRECTION

PATENT NO.   : 6,346,256
DATED        : February 12, 2002
INVENTOR(S)  : Pascal Simon It is certified that error appears in the above-identified patent and that said Letters Patent is hereby corrected as shown below:

Column 8,
Line 13, "in which $R^1$ represents a substituted or unsubstituted allyl," should read -- in which $R^1$ represents a substituted or unsubstituted alkyl --.

Column 10,
Line 21, "(II) a polyoxyallylene represented by the following" should read -- (II) a polyoxyalkylene represented by the following --.

Signed and Sealed this

Twenty-first Day of May, 2002

Attest:

Attesting Officer

JAMES E. ROGAN
Director of the United States Patent and Trademark Office